United States Patent
Olson et al.

(10) Patent No.: US 10,092,743 B2
(45) Date of Patent: * Oct. 9, 2018

(54) ANCHORS INCLUDING RIGID BODIES DEFINING FULL LENGTH SLOTS FOR USE WITH IMPLANTABLE MEDICAL LEADS

(71) Applicant: Medtronic, Inc., Minneapolis, MN (US)

(72) Inventors: Robert L. Olson, Vadnais Heights, MN (US); Thomas C. Bischoff, Minneapolis, MN (US); Michael J. Kern, St. Louis Park, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/872,975

(22) Filed: Jan. 16, 2018

(65) Prior Publication Data

US 2018/0140826 A1    May 24, 2018

Related U.S. Application Data

(60) Continuation of application No. 15/376,601, filed on Dec. 12, 2016, now Pat. No. 9,878,146, which is a division of application No. 13/357,975, filed on Jan. 25, 2012, now Pat. No. 9,517,332.

(60) Provisional application No. 61/436,990, filed on Jan. 27, 2011.

(51) Int. Cl.
*A61N 1/05* (2006.01)
*H01R 43/20* (2006.01)
*A61M 25/02* (2006.01)

(52) U.S. Cl.
CPC ............. *A61N 1/05* (2013.01); *A61N 1/057* (2013.01); *A61N 1/0558* (2013.01); *H01R 43/20* (2013.01); *A61M 2025/0293* (2013.01); *A61N 2001/0582* (2013.01)

(58) Field of Classification Search
CPC ......... A61N 2001/0582; A61N 1/0558; A61M 2025/0293; A61M 25/04
See application file for complete search history.

(56) References Cited

U.S. PATENT DOCUMENTS

| | | | |
|---|---|---|---|
| 7,591,970 B2 * | 9/2009 | Olson | A61M 25/00 264/250 |
| 2008/0275401 A1 * | 11/2008 | Sage | A61M 25/02 604/175 |
| 2009/0248054 A1 * | 10/2009 | Sage | A61M 25/02 606/174 |

* cited by examiner

*Primary Examiner* — George Evanisko
(74) *Attorney, Agent, or Firm* — Withers & Keys, LLC

(57) ABSTRACT

Anchors for use with implantable medical leads include an elastic body containing one or more rigid bodies that have longitudinal free edges. The longitudinal free edges run from end to end to define full length slots. Partial length slots may also be included within the one or more rigid bodies. The full length and partial length slots allow for deflection of the rigid bodies against the body of an implantable medical lead to hold the anchor in place on the lead. The full length slots allow a blade to pass through and cut a slit in the elastic body which allows the anchor to be removed from the lead.

12 Claims, 8 Drawing Sheets

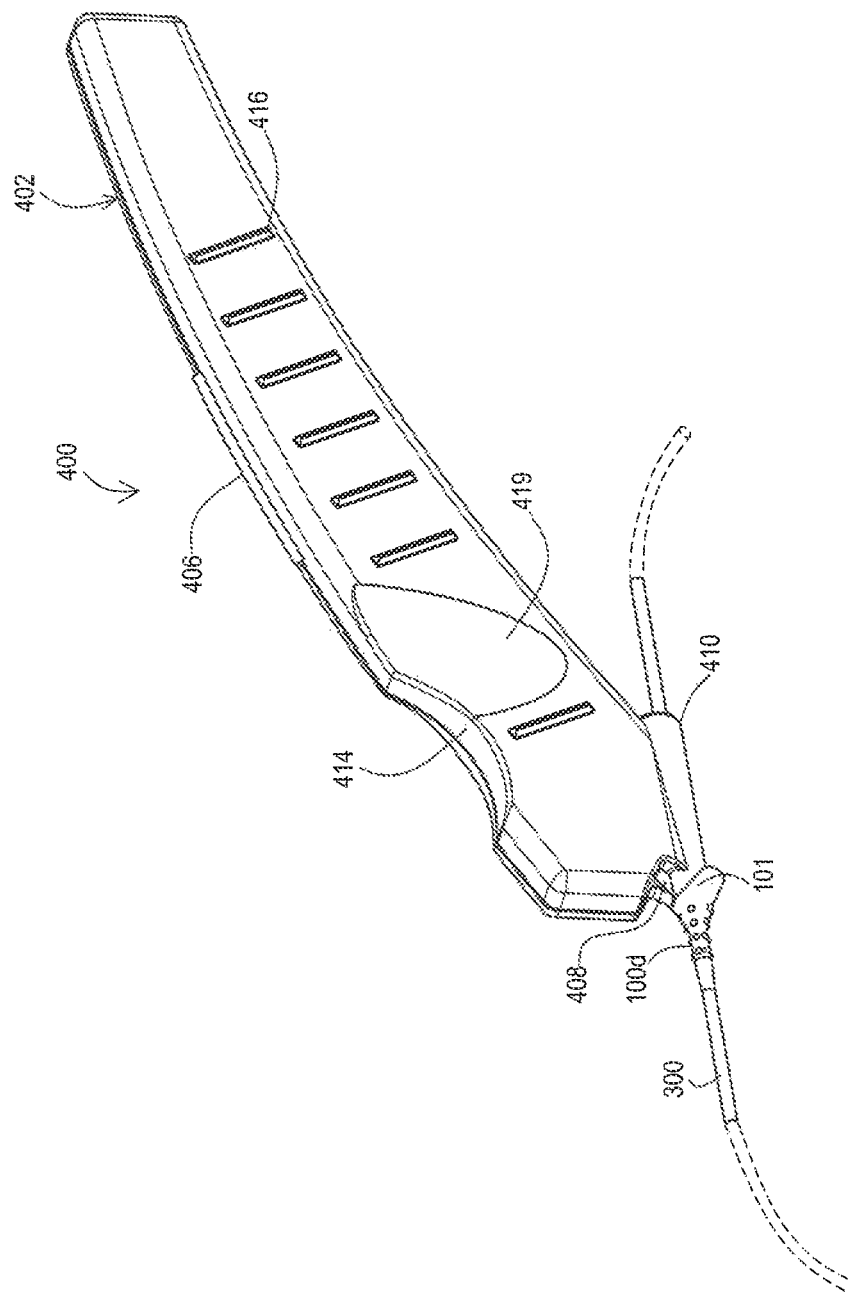

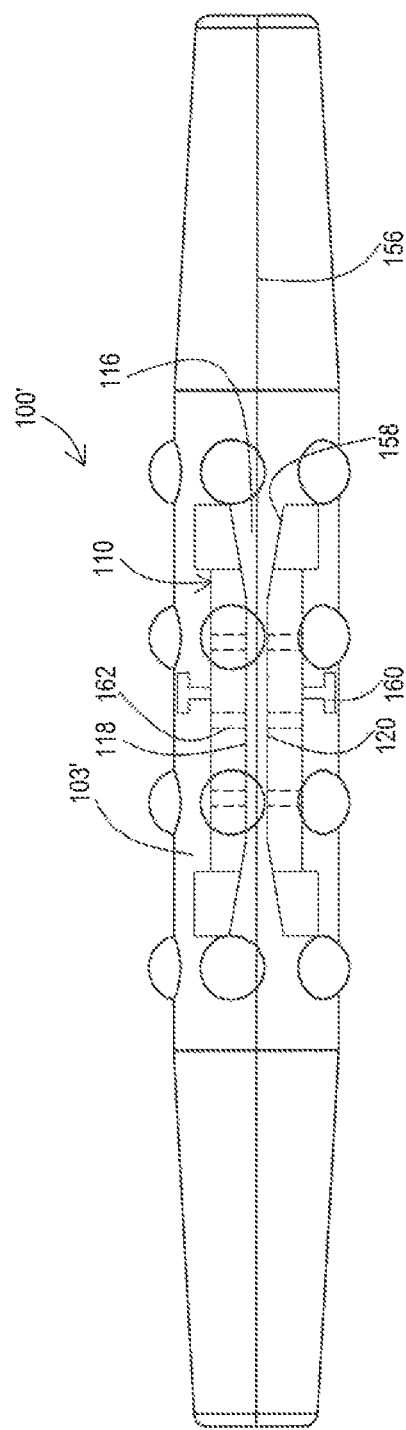

ANCHORS INCLUDING RIGID BODIES DEFINING FULL LENGTH SLOTS FOR USE WITH IMPLANTABLE MEDICAL LEADS

This application claims the benefit of U.S. Provisional Application Ser. No. 61/436,990, which was filed on Jan. 27, 2011, and is entitled "Anchors including Rigid Bodies Defining Full Length Slots for Use With Implantable Medical Leads", by Olson et al., and is incorporated herein by reference in its entirety.

TECHNICAL FIELD

Embodiments are related to anchors for implantable medical leads. More particularly, embodiments are related to anchors that include a slotted insert.

BACKGROUND

Implantable medical devices that produce stimulation signals and/or that sense physiological signals utilize implantable medical leads to carry electrical signals. The implantable medical leads include electrodes on a distal end that interface with the bodily tissue. Electrical conductors within the medical lead electrically connect the electrodes on the distal end with electrical contacts on the proximal end that engage electrical connectors of the medical device.

The medical lead is implanted within the body with the distal end being routed to the appropriate site to stimulate and/or sense. The proximal end of the lead remains nearby the incision site where the medical device is also implanted and sutured to tissue. To ensure that the lead is also held in place, an anchor is installed on the lead, and the anchor is then sutured to tissue.

Conventionally, anchors were designed to slide over the lead body and then be held tightly to the lead body by the suture. This conventional approach relied on the pressure from the suture to prevent movement of the anchor along the lead body which could be subject to reliability issues due to inadequate suturing and/or the inability of the anchor to grip the lead body even when sutured tightly.

Other conventional anchors provide a rigid but deflectable insert within an elastic body where the insert makes direct contact with the lead rather than the anchor body. Suturing the anchor causes the deflectable insert to deflect against the lead body and provide additional grip against the lead body. The insert includes partial length slots that allow for the deflection. While this approach may grip the lead better than conventional anchors that lack the insert, this approach may be vulnerable to inadequate suturing and also requires that a free end of the lead be available to remove the anchor upon removing the suturing.

SUMMARY

Embodiments address issues such as these and others by providing anchors that include one or more rigid bodies. The one or more rigid bodies provide longitudinal free edges that create one or more slots that extend from one end of the rigid body to the other end. The anchor includes an elastic body that the rigid body lies within, and the elastic body may also contact the lead body for additional grip. The anchor may be removed by slitting the elastic body at the slot of the rigid body that extends from end to end.

Embodiments provide an anchor for an implantable medical lead that includes an elastic body defining a passageway. The anchor further includes a deflectable rigid body within the passageway of the elastic body, the rigid body defining at least a portion of a lead passageway extending from a first end of the rigid body to a second end of the rigid body, the rigid body having a longitudinal free edge extending from the first end to the second end.

Embodiments provide a method of anchoring an implantable medical lead that involves sliding an anchor installation tool onto a free end of the medical lead and along the lead body until reaching a desired location on the lead body, with an anchor disposed on the anchor installation tool. The anchor includes an elastic body defining a passageway and including a deflectable rigid body within the passageway of the elastic body, the rigid body defining at least a portion of a lead passageway extending from a first end of the rigid body to a second end of the rigid body, the rigid body having a longitudinal free edge extending from the first end to the second end, the anchor installation tool being present within the lead passageway. The method further involves forcing the anchor off of the anchor installation tool and onto the lead such that the rigid body contacts the lead such that the anchor is held in position on the lead.

Embodiments provide a method of removing an anchor from an implantable medical lead, where the anchor includes an elastic body defining a passageway and includes a deflectable rigid body within the passageway of the elastic body. The rigid body defines at least a portion of a lead passageway extending from a first end of the rigid body to a second end of the rigid body, and the rigid body has a longitudinal free edge extending from the first end to the second end with the lead being present within the lead passageway. The method involves removing the anchor by cutting a slit through the elastic body of the anchor adjacent to the longitudinal free edge.

DESCRIPTION OF THE DRAWINGS

FIG. 11 shows removal of an example of the anchor including the rigid body with a longitudinal free edge.

FIG. 12 shows an example of an anchor including the rigid body with the longitudinal free edge and additional features.

DETAILED DESCRIPTION

Embodiments provide anchors for implantable medical leads that include a deflectable rigid body within an elastic body. The rigid body includes a longitudinal free edge which aids in allowing deflection of the rigid body and also creates a place where a blade may pass through the elastic body to cut a slit through the elastic body to allow for removal of the anchor from the lead.

Figure 1:
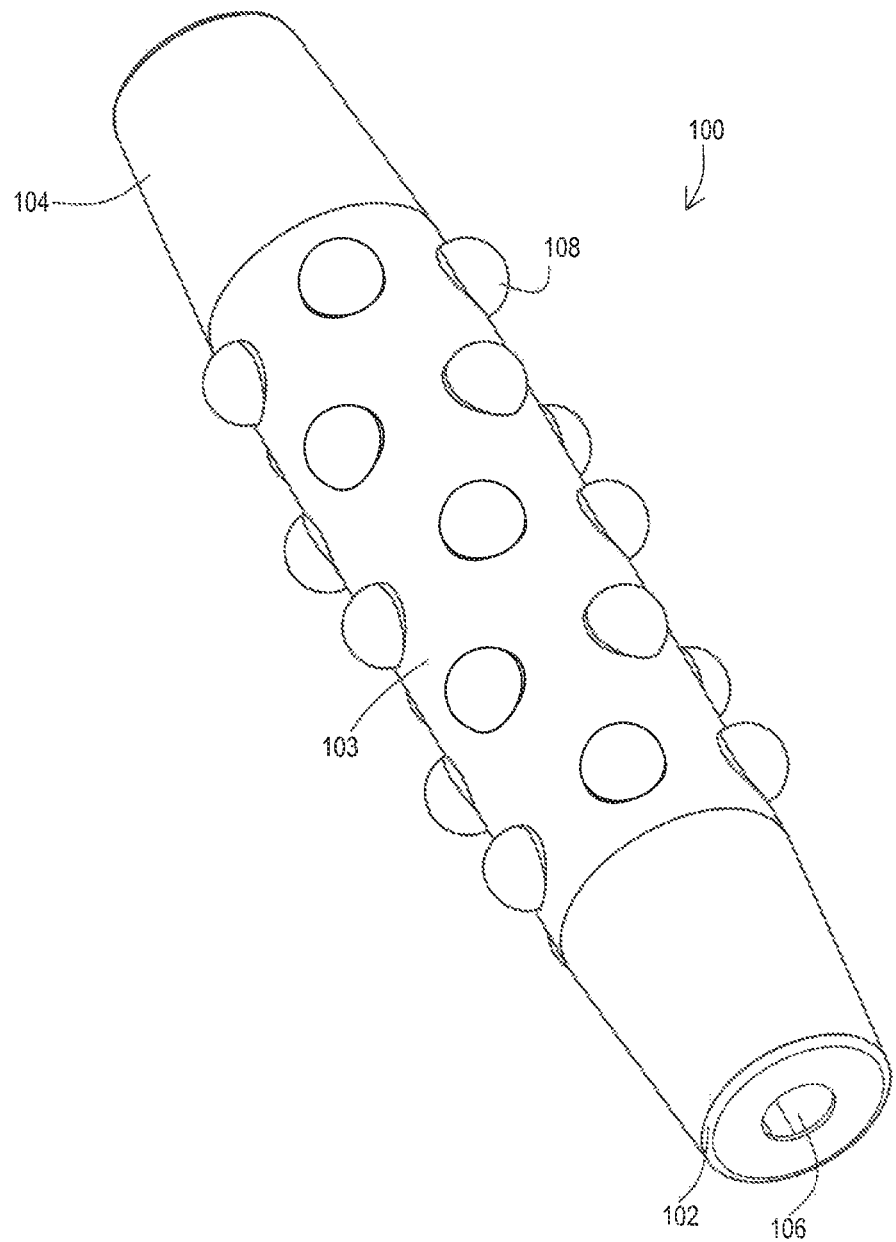
FIG. 1 shows a perspective view of one example of an anchor that includes a rigid body insert.

FIG. 1 shows an example of an anchor 100. The anchor 100 includes an elastic body 103 that has a first end 102 and a second end 104. The elastic body 103 may be constructed of various elastic materials such as silicone rubber or other polymers with silicone end groups. The elastic body 103 defines a passageway 106 that a medical lead may pass through. In this particular example, the passageway 106 of the elastic body 103 may be sized such that the elastic body 103 contacts the lead to provide additional grip for holding the anchor 100 in a fixed position on the lead. Additionally, in this example the ends 102, 104 taper to smaller diameters.

The anchor 100 may include additional external features. For instance, this example provides a collection of protrusions 108 that are distributed about a central section of the elastic body 103 between the two tapered ends 102, 104. These protrusions may provide additional resistance against the tissue within the patient to assist in reducing movement of the lead within the patient.

Figure 2:
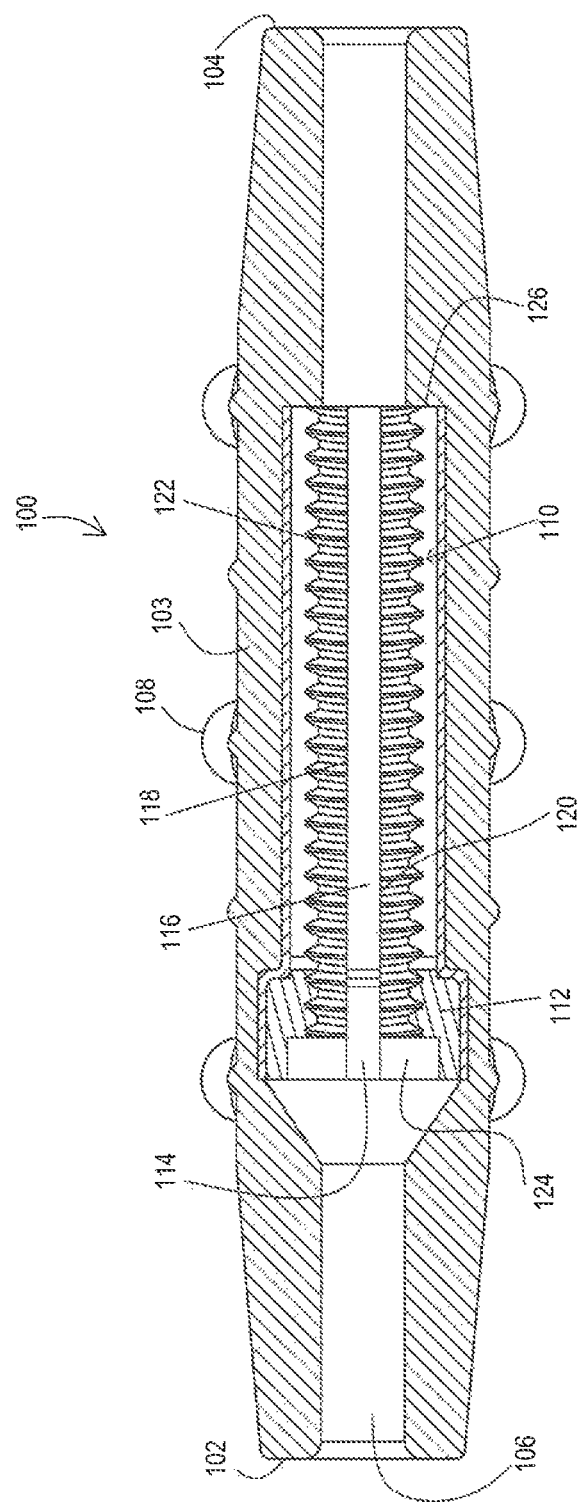
FIG. 2 shows a cross-sectional view of the anchor example showing the presence of at least one rigid body having a longitudinal free edge.

FIG. 2 shows a cross-section of this example of the anchor 100. Here the presence of at least one rigid body 110 can be seen positioned within the passageway 106 of the elastic body 103. The elastic body 103 may be molded over the rigid body 110. Furthermore, the elastic body 103 may be molded such that the elastic body 103 exerts a compression force against the rigid body 110 to deflect the rigid body 110 against a lead when the anchor is installed. Additionally or alternatively, the rigid body 110 itself may be biased to a diameter smaller than the lead body so as to deflect against the lead when installed, particularly where there is a single rigid body 110 that is present. The installation is discussed in more detail below with reference to FIGS. 8-10.

The rigid body 110 may be constructed of various materials such as titanium, tungsten, stainless steel, tantalum, polyether ether ketone, MP35N® alloy, urethane, epoxy, sulfone, nylon and the like. Where a single rigid body 110 is present, the rigid body 110 may have two circumferentially spaced longitudinal free ends 118 and 120 that extend from one end 124 to another end 126 of the rigid body. These longitudinal free ends 118 and 120 represent a circumferential break through the rigid body into a lead passageway 114 defined by the rigid body 110. Accordingly, these longitudinal free ends 118 and 120 define a slot 116 that extends from the exterior of the rigid body 110 to the interior lead passageway 114.

In this particular example, the rigid body 110 has an inner surface that includes ridges 122 that are at an angle relative to the longitudinal axis of the lead passageway 114. These ridges 122 may contact the lead body and provide a source of increased friction that resists movement of the anchor 100 in the longitudinal direction. The diameter of the passageway 106 at the ends 102 and 104 of the elastic body 103 can be seen to be similar to the diameter of the lead passageway 114 defined by the rigid body 110 as the lead will pass through both the passageway 106 and the lead passageway 114. The elastic body 103 of this example is sized to contact the lead at the ends 102, 104 where the rigid body 110 is not present.

In this particular example, the rigid body 110 includes an area 112 having a larger outer diameter and thus a larger radial thickness. In this example, the larger diameter area 112 is located, at the end 124. This larger diameter area 112 creates additional interference between the elastic body 103 and the rigid body 110 so as to better hold the elastic body 103 in place relative to the rigid body 110 which ultimately assists in holding the anchor 100 as a whole in place relative to the lead.

Figure 3:
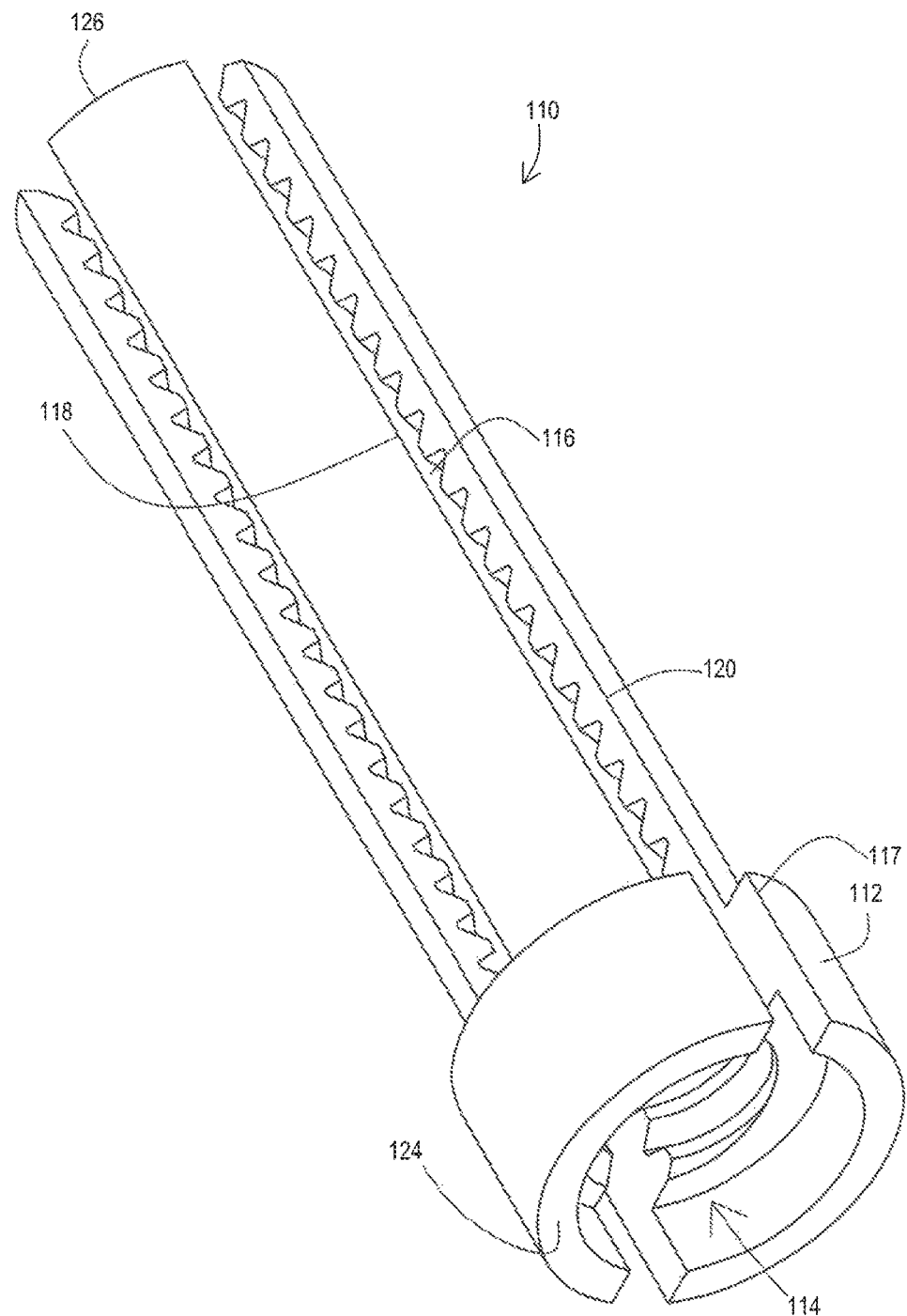
FIG. 3 shows a perspective view of one example of at least one rigid body that has a longitudinal free edge.
Figure 4:
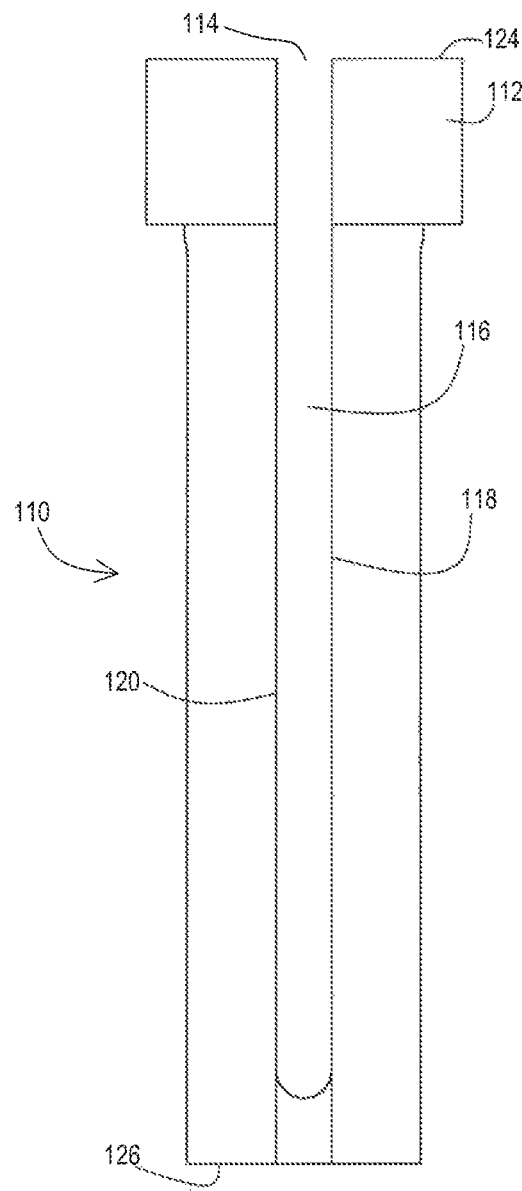
FIG. 4 shows a side view of at least one rigid body example having at least one longitudinal free edge.

As discussed below, the rigid body 110 may be the only rigid body present to define the lead passageway 114 or may be accompanied by one or more additional rigid bodies. FIGS. 3 and 4 show additional views of one example of the rigid body 110. In this example, the rigid body 110 includes the longitudinal free edges 118 and 120 that run from end 124 to end 126 to define the full length slot 116. However, to aid in deflection, the rigid body 110 also includes one or more partial length slots 117. In this case, the slot 117 stops at the larger area 112 rather than continuing to the end 124. It will be appreciated that the partial length slot could terminate at other locations along the length of the rigid body 110 such as nearby the opposite end 126.

The full length slot 116, as well as the partial length slots 117, allows the rigid body to be deflected. For instance, it may be desirable that the elastic body 103 deflects the rigid body 110 so as to force the rigid body 110 against the lead for increased friction and stability. Where a single rigid body is present that encircles the lead passageway 114 of FIG. 2, the partial length slots 117 may aid in removing the anchor from the lead by allowing it to be deflected outward after the elastic body 103 has been cut where the elastic body is present at the slot 116 by a user pulling the slot 116 to a more open position such that the lead can escape.

FIG. 3 may also represent two rigid bodies where a slot 180 degrees from the slot 116 is also a full length slot. In that case, two full length slots 116 as well as one or more partial length slots 117 may be present to allow the rigid bodies to be deflected by the elastic body 103. Also in the case of multiple rigid bodies defining the lead passageway 114, upon cutting the elastic body 103 where the elastic body 103 is present at the slot 116, the separate rigid bodies naturally separate as the elastic body 103 separates at the slit so that the lead can escape.

Figure 5:
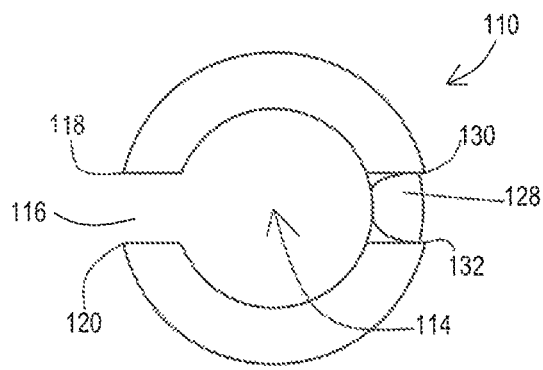
FIG. 5 shows an end view of an example of a single rigid body where longitudinal free edges create a slot.
Figure 6:
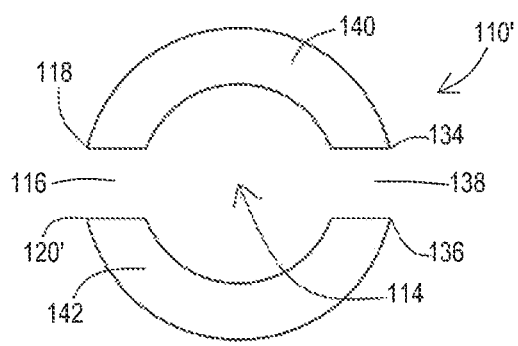
FIG. 6 shows an end view of an example of two rigid bodies where each rigid body provides a longitudinal free edge such that two slots are provided.
Figure 7:
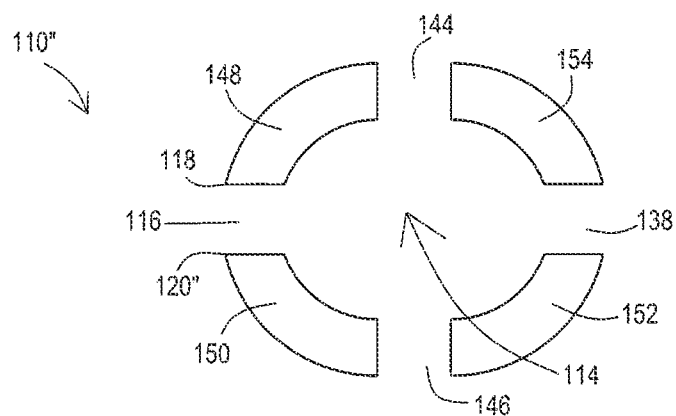
FIG. 7 shows an end view of an example of four rigid bodies where each rigid body provides a longitudinal free edge such that four slots are provided.

FIGS. 5-7 illustrate end views of various examples of one or more rigid bodies that may be present within the elastic body 103. FIG. 5 shows the example of a single rigid body 110 having two longitudinal free edges 118 and 120 that are circumferentially spaced from one another. In this example, the single rigid body 110 surrounds the lead passageway 114 except for the area of the slot 116. It will be appreciated that when a single rigid body 110 is present, the rigid body 110 may surround the lead passageway 114 by lesser amounts than is shown in FIG. 5. For example, the rigid body 110 may only encircle the lead passageway by 180 degrees or by only 90 degrees or to various other degrees. In each of these cases, the rigid body 110 may still contact the lead body within the lead passageway 114 to provide additional resistance. When the elastic body 103 is slit in the area of the slot 116, the rigid body 110 may be pulled open to widen the slot 116 and allow the lead body to escape by lateral movement of the lead or the anchor.

In the example of FIG. 5, the single rigid body 110 also includes at least one partial length slot 128 defined by longitudinal free edges 130 and 132. However, as this is a partial length slot, these longitudinal free edges 130, 132 do not extend completely from end to end of the rigid body 110.

FIG. 6 shows an example of two distinct rigid bodies 140, 142 forming a structure 110' that may be present within the elastic body 103 so as to encircle the lead passageway 114. The rigid body 140 includes the longitudinal free edges 118 and 134 that extend from end to end while the rigid body 142 includes the longitudinal free edges 120' and 136 that extend from end to end. Thus, the rigid body 140 and 142 having adjacent longitudinal free edges that are circumferentially spaced and cooperate to create the full length slots 116 and 138. These two rigid bodies 140, 142 may be deflected toward the lead body by the elastic body 103 to create increased resistance. Furthermore, upon the elastic body 103 being slit in the area of either the slot 116 or the slot 138, the opposite slot allows the two rigid bodies 140, 142 to naturally deflect outward away from the lead body to allow the lead body to escape by lateral movement of the lead or the anchor.

FIG. 7 shows an example of four distinct rigid bodies 148, 150, 152, and 154 forming a structure 110'' that may be present within the elastic body 103 so as to encircle the lead passageway 114. Each of the rigid bodies 148, 150 152, and 154 provide longitudinal free edges that extend from end to end so as to create four full length slots 116, 138, 144, and 146. For instance, the longitudinal free edge 118 of the rigid body 148 is circumferentially spaced from the longitudinal free edge 120'' of the rigid body 150 so as to define the slot 116. These four rigid bodies 148, 150, 152, and 154 may be deflected toward the lead body by the elastic body 103 to create increased resistance. Furthermore, upon the elastic body 103 being slit in the area of any of the slots 116, 118, 144, or 146, the opposite slot allows the four rigid bodies 148, 150, 152, and 154 to naturally deflect outward away from the lead body to allow the lead body to escape by lateral movement of the lead or the anchor.

Figure 8:
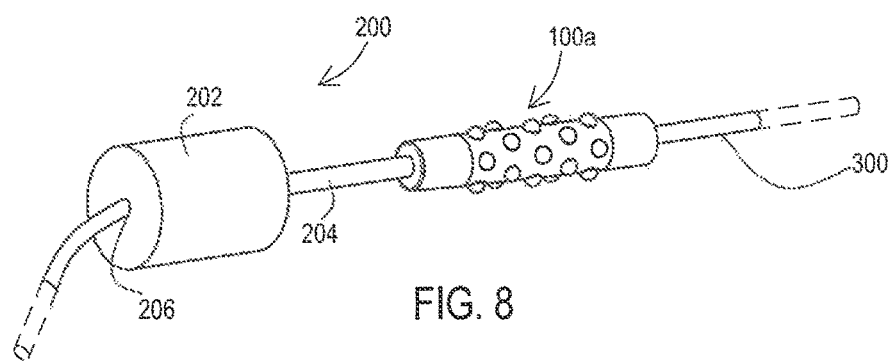
FIG. 8 shows a first stage of installing an example of the anchor including the rigid body with a longitudinal free edge.
Figure 9:
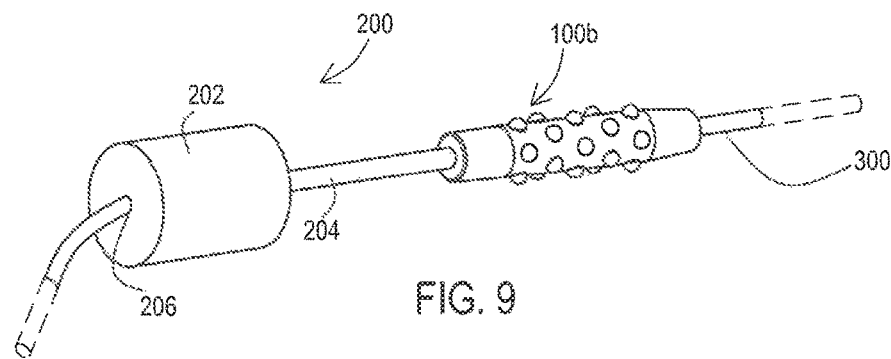
FIG. 9 shows a second stage of installing an example of the anchor including the rigid body with a longitudinal free edge.
Figure 10:
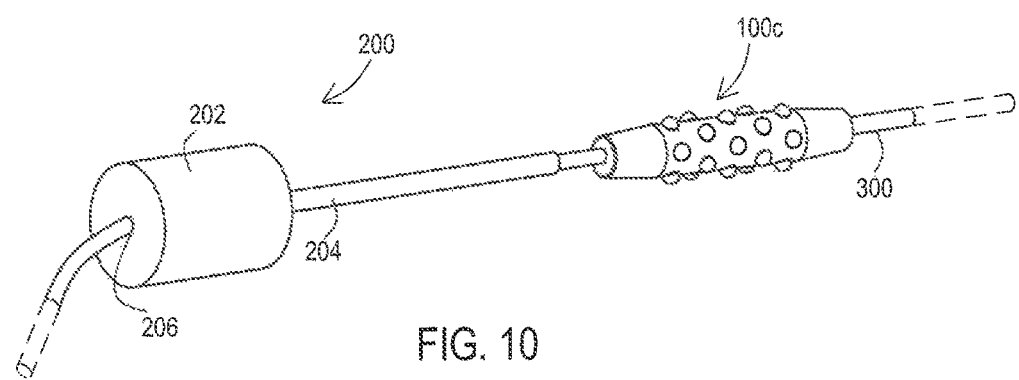
FIG. 10 shows a third stage of installing an example of the anchor including the rigid body with a longitudinal free edge.

FIGS. 8-10 illustrate one example of an installation process for the anchor 100. In FIG. 8, a first phase of the installation process shows a first configuration of the anchor 100a. Here, the anchor 100a is installed on a shaft 204 of an installation tool 200. Typically, the shaft 204 is constructed of a metal or other rigid material that the insert, will not overly grip such that the anchor 100a can be moved along the shaft 204. The tool 200 also includes a handle 202 mounted to the shaft and a lead passageway 206 that passes through the handle 202 and the shaft 204. The tool 200 with the anchor 100a thereon is installed onto the lead 300 by passing the lead 300 through the lead passageway. Upon reaching a point where the anchor is to be located, the user forces the anchor 100a to begin to slide off of the shaft 204 such as by gripping the anchor to move it.

FIG. 9 shows a second stage of installation and a second configuration of the anchor 100b. Here, a first end of the anchor 100b is now off of the shaft 204 and in position on the lead 300. The first end of the anchor 100b may be gripping the lead 300.

FIG. 10 shows a third stage of installation and a third configuration of the anchor 100c. Here, the anchor 100c has been completely forced off of the shaft 204 and is entirely located on the lead 300 at the intended location. At this point, the one or more rigid bodies 110 within the anchor 100c are gripping the lead 300. Furthermore, the ends of the elastic body 103 of the anchor 100c may also be gripping the lead 300. The clinician may then suture the anchor 100c to the adjacent body tissue while relying on the anchor 100c to maintain its position on the lead 300.

In some cases, there may be a need to remove the anchor from the lead 300, such as where the lead 300 needs to be removed or where the lead 300 needs to have freedom of movement while being disconnected from on medical device and then reconnected to another. In such a case, rather than attempting to slide the anchor 100c off of a free end of the lead after having removed the sutures, the anchor 100c may be cut free from the lead.

The anchor 100c may be cut free from the lead 300 by one of various methods. For instance, a surgeon may cut through the elastic body by cutting along the slot 116 which is adjacent to the longitudinal free edges 118, 120. To do so, the surgeon may use a cutting tool such as a scalpel and carefully cut a slit through the elastic body 103 by passing the blade along the slot 116 or other slot that may be present while trying to avoid cutting into the lead 300.

Where the anchor 100c includes one rigid body 110, such as is shown in FIG. 5, where only a single full length slot is present, the surgeon may use this technique because as the anchor 100c is cut, the single rigid body 110 may prevent the anchor from opening to the extent anything such as a cutting tool that is wider than the slot 116 would pass through. With a scalpel, there is no tool portion other than the blade that passes through the slot 116 so there is no interference issue. In this case, once the elastic body has been cut from end to end, the surgeon may then pry open the rigid body so that the slot 116 becomes wide enough to allow the lead 300 to pass through the widened slot 116 by lateral movement of the lead 300.

For embodiments where the anchor 100c includes a single rigid body that creates a relatively wide slot or includes multiple rigid bodies and hence multiple full length slots, cutting the elastic body along one of the full length slots such as slot 116 allows the multiple rigid bodies to separate along with the elastic body such that the slot 116 widens where the elastic body has been cut. Therefore, a cutting tool such as an anchor removal tool 400 like that shown in FIG. 11 may be used. Some examples of cutting tools are further shown and described in the appendix A included herewith.

As shown in FIG. 11, the anchor removal tool 400 of this example includes a body 402 forming a handle that may be grasped by the user. The tool 400 includes features to aid in gripping the handle 402, such as protrusions 416 and indentations 414 and 419. The tool 400 includes a guide portion 410 having a lead passageway that the lead 300 is introduced into and passes through as the tool 400 is forced to slide along the lead 300 to cut a slit through the elastic body 103 of the anchor 100d shown in a partially cut configuration.

To place the lead 300 into the lead passageway of the guide portion 410, the lead may be inserted by passing a free end of the lead 300 axially into the front of the guide portion 410. Alternatively, to avoid using and end of the lead 300 which may not be readily available, the handle 402 may have a moving part such as a second half connected via a hinge 402 that opens the guide portion 410 longitudinally so that the lead 300 may be inserted by laterally moving the lead into the lead passageway of the open guide portion 410 at any point along the lead 300. The guide portion 410 may then be closed to contain the lead 300. Details of opening and closing the guide portion 410 are discussed in more detail in the provisional U.S. Provisional Patent Application No. 61/436,986, filed on Jan. 27, 2011, entitled "Tools and Methods for Removing Anchors from Medical Leads" and also in co-pending U.S. patent application Ser. No. 13/356, 050, filed Jan. 23, 2012, entitled "Tools and Methods for Removing Anchors from Medical Leads", each of which is incorporated by reference in its entirety as if re-written herein.

Once the lead 300 is within the guide portion 410, the tool 400 is forced to slide along the lead 300 and contact the anchor 100d. A blade 408 of the tool 400 that forms a plane that intersects with the guide portion 410 contacts the anchor 100d and cuts through the elastic body. The blade 408 is steered through a slot, such as slot 116, formed by the rigid bodies as it cuts through the elastic body 103. As the elastic body 103 is cut, the cut portion 101 of the elastic body 103 begins to fall away from the lead, particularly where there are multiple rigid bodies. Once the tool 400 has cut all the way through the elastic body 103 from end to end of the anchor 100d, the anchor 100d is free from the lead 300. To the extent the anchor 100d is sutured during the use of the tool 400, the cutting tool 400 may also cut through the sutures.

FIG. 12 shows additional features of an anchor 100' that may be included to aid in the removal of the anchor 100'. In order to cut through the anchor 100' to remove it, the blade passes through one of the full length slots such as slot 116 so that the rigid body 110 does not block the blade. In order to steer the blade through the slot, without visual aids the clinician may begin cutting until encountering the rigid body, then try to steer the blade to either side of the anchor 100 to try to eventually get the blade into a slot. However, the anchor 100' may include an elastic body 103' that is transparent, while the rigid body 110 is opaque, such that the clinician can see the slot 116 and can steer the blade directly into the slot. Additionally or alternatively, the anchor 100' may include a stripe 156 that is visible and that is present on the elastic body 103' and in alignment with the slot. Thus, the clinician can steer the blade along the stripe 156 so as to pass the blade through the slot 106 to successfully cut through and remove the anchor 100'.

Additional features may also be provided in one or more embodiments. For instance, to further assist the user in guiding the blade into the slot 116, as an alternative to or in addition to the stripe 156 and/or transparent elastic body 103', the longitudinal free edges of the rigid body 110 that define the slot 116 may have angled ends 158. These angled ends 158, which may be at either end or at both ends of the rigid body 110, may provide a funnel-like feature that assists in guiding a cutting blade into the slot 116 when the cutting blade is not already aligned with the slot 116.

Other additional features that may be provided in one or more embodiments include stabilizing features such as barbs 160 that may be formed, machine, or attached to the rigid body 110. These stabilizing features extend upward into the elastic body 103' to further maintain the position of each rigid body 110 that may be present relative to the elastic body 103' and relative to other rigid bodies that may be present within the elastic body 103'. Additionally or alternatively, the rigid body 110 may include cross-holes 162, shown in phantom as they are otherwise hidden in this view, which allows the elastic material of the body 103' to infiltrate the cross-holes 162 and further stabilize the rigid body pieces 110. Also, the flange 112 is shown on both ends of this example to further assist in stabilizing the rigid body 110 within the elastic body 103' but may alternatively be at one end or the other or may be omitted.

While embodiments have been particularly shown and described, it will be understood by those skilled in the art that various other changes in the form and details may be made therein without departing from the spirit and scope of the invention.

What is claimed is:

1. A method of anchoring an implantable medical lead, comprising:
sliding an anchor installation tool having a shaft with an end affixed directly to a larger diameter cylindrical handle with the handle being in a fixed position relative to the shaft onto a free end of the medical lead and along a lead body of the medical lead until reaching a desired location on the lead body, where the shaft and handle have parallel longitudinal axes, with an anchor disposed on the shaft of the anchor installation tool, the anchor including an elastic body defining a passageway and including a deflectable rigid body within the passageway of the elastic body, the rigid body defining at least a portion of a lead passageway extending from a first end of the rigid body to a second end of the rigid body with the second end being a most distal end of the rigid body, the first end and the second end defining radial surfaces in a plane perpendicular from an axial dimension of the passageway with the first end having a shoulder that creates a larger diameter than the second end, the elastic body engaging the radial surface of at least the second end, the rigid body having an inner surface facing radially inward toward the lead passageway and extending from the first end to the second end of the rigid body, the entire inner surface being exposed to the lead passageway from the first end to the second end, the rigid body having a longitudinal free edge extending from the first end to the second end over the entire length of the rigid body, the longitudinal free edge being an edge of a surface at an outermost radial position of the rigid body, the longitudinal free edge having a first portion at the outermost radial position that is parallel to an axial dimension of the passageway and having a second portion extending axially from the first portion to the first end of the rigid body at the outermost radial position and to a different circumferential position to form an angle greater than zero and less than 90 degrees in a circumferential direction relative to the axial dimension of the passageway and having a third portion extending axially from the first portion to the second end of the rigid body at the outermost radial position and to a different circumferential position to form an angle greater than zero and less than 90 degrees in a circumferential direction relative to the axial dimension of the passageway, the shaft of the anchor installation tool being present within the lead passageway; and
moving the anchor from the shaft of the anchor installation tool to the lead.

2. The method of claim 1, wherein upon moving the anchor from the anchor installation tool, the elastic body contacts the lead.

3. The method of claim 1, wherein the elastic body deflects the rigid body to affect the contact of the rigid body with the lead.

4. The method of claim 1, further comprising removing the anchor by cutting a slit through the elastic body of the anchor adjacent to the longitudinal free edge.

5. The method of claim 4, wherein the elastic body is transparent at least in an area adjacent the longitudinal free edge of the rigid body, the method further comprising viewing the adjacent longitudinal free edge through the transparent elastic body to align a cutting tool to be adjacent and parallel to the longitudinal free edge when removing the anchor.

6. The method of claim 4, wherein a stripe is present on the elastic body adjacent the longitudinal free edge of the rigid body, the method further comprising aligning a cutting tool relative the stripe when removing the anchor.

7. The method of claim 1, wherein the rigid body further comprises a second longitudinal free edge extending from the first end to the second end.

8. The method of claim 7, wherein the longitudinal free edge is circumferentially spaced from the second longitudinal free edge to form a slot in the rigid body that extends from the first end to the second end.

9. The method of claim 1, further comprising a second deflectable rigid body within the passageway of the elastic body, the second rigid body defining at least a portion of the lead passageway extending from a first end of the second rigid body to a second end of the second rigid body, the second rigid body having a longitudinal free edge extending from the first end to the second end of the second rigid body.

10. The method of claim 9, wherein the longitudinal free edge of the rigid body is circumferentially spaced from the longitudinal free edge of the second rigid body to form a slot that extends from the first end of the rigid body and the first end of the second rigid body to the second end of the rigid body and the second end of the second rigid body.

11. The method of claim 1, wherein the lead passageway is defined by an inner surface of the rigid body that includes ridges that are angled relative to a longitudinal axis of the lead passageway, and wherein the ridges grip the lead once the anchor is moved to the lead.

12. The method of claim 1, wherein the rigid body has a greater radial thickness at the first end than at the second end, wherein the elastic body includes a plurality of protrusions on an exterior surface, and wherein the elastic body includes tapered first and second ends.

* * * * *